United States Patent [19]
Rinse

[11] 4,022,725
[45] May 10, 1977

[54] CONDENSED OLIGOMERIC ORGANO METALLIC RESINOUS ACYLATES CONTAINING LIGANDS OF MONOBASIC CARBOXYLIC ACID OF AT LEAST 7 CARBON ATOMS AND BRIDGING RADICALS OF DIVALENT CARBOXYLIC ACIDS OF AT LEAST 6 CARBON ATOMS AND PROCESSES FOR PRODUCING SUCH RESINS

[75] Inventor: Jacobus Rinse, East Dorset, Vt.

[73] Assignee: MOACO Metal Oxide Acylates Company, Laussanne, Switzerland

[22] Filed: Apr. 1, 1975

[21] Appl. No.: 564,040

Related U.S. Application Data

[63] Continuation-in-part of Ser. No. 312,264, Dec. 4, 1972, and a continuation-in-part of Ser. No. 77,341, Oct. 1, 1970, abandoned, which is a continuation-in-part of Ser. No. 840,604, July 7, 1969, Pat. No. 3,634,476.

[52] U.S. Cl. .............................. 260/18 R; 260/2 M; 260/414; 260/439 R
[51] Int. Cl.² .......................................... C08L 85/00
[58] Field of Search ............... 260/2 M, 18 R, 97.5, 260/414, 439 R

[56] References Cited
UNITED STATES PATENTS

| 2,477,116 | 7/1949 | Cowan et al. | 260/414 |
| 2,584,041 | 1/1952 | Nowak et al. | 260/97.5 |
| 2,599,553 | 6/1952 | Hotten | 260/414 |
| 2,620,345 | 12/1952 | Dean | 260/414 |
| 3,546,262 | 12/1970 | Rinse | 260/414 |

FOREIGN PATENTS OR APPLICATIONS

| 1,081,940 | 9/1967 | United Kingdom | 260/414 |

OTHER PUBLICATIONS

Cowan et al., Ind. & Engr. Chem., vol. 36, No. 2, pp. 148–151, Feb. 1944.

*Primary Examiner*—M. J. Welsh
*Attorney, Agent, or Firm*—Littlepage, Quaintance, Murphy, Richardson & Webner

[57] ABSTRACT

Oligomeric organo metallic resins which are divalent metal acylates of the formula: X M D M X, wherein each X is an acyloxy ligand of a monobasic acid containing at least 7 carbon atoms; D is a diacyloxy radical (ligand) of a dibasic acid containing at least 6 carbon atoms; and M is a divalent metal atom other than calcium are provided. These novel oligomeric resins are particularly suitable as coating compositions and when they contain oxidizable divalent metals are especially rapid drying.

16 Claims, No Drawings

CONDENSED OLIGOMERIC ORGANO METALLIC RESINOUS ACYLATES CONTAINING LIGANDS OF MONOBASIC CARBOXYLIC ACID OF AT LEAST 7 CARBON ATOMS AND BRIDGING RADICALS OF DIVALENT CARBOXYLIC ACIDS OF AT LEAST 6 CARBON ATOMS AND PROCESSES FOR PRODUCING SUCH RESINS

RELATED APPLICATIONS

This application is a continuation-in-part of my copending application Ser. No. 312,264, filed Dec. 4, 1972, which was copending with and a continuation-in-part of my application Ser. No. 77,341, filed Oct. 1, 1970, (now abandoned), which in turn was a continuation-in-part of my application Ser. No. 840,604, filed July 7, 1969, now Pat. No. 3,634,476, issued Jan. 11, 1972.

BACKGROUND OF THE INVENTION

During the last 20 years, I have produced oligomeric or condensed organo metal compounds of a resinous nature, namely, metal-oxide acylates (MOA) of substantially all metals having a valency of more than 1. Most of the oligomeric or condensed resinous compounds were first produced by me. Many of these compounds have been patented. In my U.S. Pat. No. 3,546,262, patented Dec. 8, 1970, which is most relevant to the instant invention, I mention a number of these patents. My U.S. Pat. No. 3,546,262 relates to divalent metal oxide acylates (DMOA) and this invention may be considered a modification of that invention in the sense that the same process may be used and in the additional sense that the bridging oxygen atom is replaced by a ligand, or radical, of a divalent carboxylic acid of 6 or more carbon atoms (D). It will be understood the ligand or radical of a divalent carboxylic is the rest, or remainder, of a dicarboxylic acid after the removal or replacement of the two hydrogens of the two carboxyl groups of the divalent acid.

Since the issuance of U.S. Pat. No. 3,546,262, three other patents have issued in my name, namely U.S. Pat. 3,625,934 of Dec. 7, 1971; U.S. Pat. No. 3,634,476 of January 11, 1972; U.S. Pat. No. 3,673,229 of June 27, 1972. The second of the above mentioned patents, namely U.S. Pat. No. 3,634,476 is particularly relevant to the present invention, for it emphasizes the strenous reaction conditions necessary to produce the organometal resinous compounds of this invention and the advantageous use of liberating agents.

Generally speaking, DMOA's of my first mentioned patent are produced by reacting an uncondensed acylate of a divalent metal derived from a low molecular monovalent carboxylic acid of not more than 5 carbon atoms, such as for instance, ferrous acetate, with a high molecular monovalent carboxylic acid containing at least 7 carbon atoms, such as stearic acid, under severe reaction conditions with the aid of a liberating agent, as also emphasized in said patent. Also, as pointed out in said first mentioned patent, and in other patents, it is not necessary to use preformed uncondensed divalent metal acylates of low molecular carboxylic acids for the reaction conditions used are sufficiently strenuous to form such low molecular uncondensed acylates in situ from the metal per se, the metal oxides, metal carbonates or metal hydroxides. Thus, in referring to uncondensed divalent metal acylates of low molecular monovalent carboxylic acids, I have reference to such uncondensed acylates per se or those formed in situ.

Also, as disclosed in my copending Application Ser. No. 312,264, filed Dec. 4, 1972, I have disclosed it is not necessary to use higher molecular monovalent carboxylic acids with more than 7 carbon atoms per se, but also such acids esterified with a low molecular volatile alcohol such as those containing 2–5 carbon atoms may be used conjointly. These alcohols are volatile in the sense that they are more volatile than the monovalent carboxylic acid containing 7 or more carbon atoms. Likewise, such esters of monovalent carboxylic acid can be used in the process hereof. However, the dibasic carboxylic acids are used per se.

Consistent with prior usage, "acyloxy" and "acylate" are used interchangeably and the ligand of a carboxylic acid is the "rest" or radical remaining when the H or the H's of the carboxylic acid is replaced or removed.

SUMMARY OF THE INVENTION

As pointed out in detail in the patent first mentioned above, a detailed process is set out for producing oligomeric organometal resinous compounds of divalent metals (DMOA) having the formula: X M O M X, wherein M is a divalent metal and each X is an acyloxy ligand, the acyl of which is selected from the group consisting of carboxylic acid acyl and dialkyl phosphoric acid acyl; each carboxylic acid acyl containing at last 6 carbon atoms and preferably 7 carbon atoms and each alkyl radical containing at least 5 carbon atoms. In particular, the divalent metals disclosed are zinc, lead, copper, cobalt, manganese, calcium, cadmium, barium, strontium and divalent tin, iron and chromium.

This invention may be most easily visualized by stating that the bridging oxygen atom in my first mentioned patent is replaced with a divalent radical or ligand of a dibasic carboxylic acid containing at least 6 carbon atoms. In a preferred embodiment of the invention, this divalent ligand is derived from dimer linoleic acid.

This replacement may be achieved by reacting the resinous oligomers, or condensed organo metal acylates, of U.S. Pat. No. 3,546,262 under the conditions there set out with an appropriate dibasic carboxylic acid containing at least 6 carbon atoms. While no theory of the invention is necessary to an understanding thereof, the reaction may be considered to take place substantially as indicated below.

XMOMX + HOOCRCOOH + XMOMX → XMOH + XMOOCRCOOMX + XMOH → XMOMX + H$_2$O + XMDMX.

The completion of the reaction may be determined in the manner set out in my previously issued patents. In this formula, X is a ligand of a monovalent carboxylic acid of at least 7 carbon atoms and D is a ligand, or radical, of a dibasic carboxylic acid of at least 6 carbon atoms and advantageously is a ligand of dimer linoleic acid. In other words, D is — OOCRCOO — wherein R contains at least 6 carbon atoms and preferably is an aliphatic or carboxylic hydrocarbon radical of 6 or more atoms.

It will be observed that in acordance with the above noted formula, the number of higher molecular monovalent carboxylic acid ligands is four times the number of higher molecular divalent ligands. In this way you would have a mixture of equal proportions of the novel compounds of this invention and the novel compounds of the patent first mentioned herein. If one were desirous of converting all of DMOA's to XMDMX compounds, it would only be necessary to use only twice the molar proportions of monovalent carboxylic acids relative to the number of mols of divalent carboxylic acids.

However, in accordance with a preferred embodiment of the invention, the divalent carboxylic acids are included as a reactant together with the other reactants in the process set out in my U.S. Pat. No. 3,546,262. Preferably these divalent reactants are present in a molar proportion of 1:2 relative to the monovalent high molecular carboxylic acid reactants containing at least 7 carbon atoms. Apparently due to the greater affinity of divalent carboxylic acids for the metals as compared to the monovalent carboxylic acids, the divalent carboxylic acids will preferentially form a bridging radical rather than having the oxygen as the bridging radical. Putting it another way, the bridging O is replaced with a bridging D.

In my study of the reactions hereof, I have discovered that the divalent carboxylic acids have a greater affinity for the divalent metals than the monobasic carboxylic acids. Thus, if the relative molar proportions of divalent carboxylic acids are in excess of 1:2 in comparison to the molar proportions of the monovalent higher molecular carboxylic acids, the chain will grow in accordance with the formula XMDMDMDMX, or the like. In general, this type of reaction is not preferred, for such compounds are too high in molecular weight and too difficult to dissolve and handle technically, especially when used as protective or decorative coatings or the like. However, they do have other utilities.

On the other hand, there is no disadvantage in using molar ratios of higher molecular dibasic carboxylic acids relative to the quantity of monovalent dicarboxylic acid lesser than 1:2. Under such circumstances, one obtains a mixture of the compounds with the formula: XMOMX and XMDMX. At times this is even advantageous. However, as stated above, it is possible to convert all of the compounds into compounds having the formula: XMDMX by using the higher molecular divalent carboxylic acid reactant and the monovalent higher molecular carboxylic acids reactant in a molar ratio of approximately 1:2. The molar ratios are approximate and may be readily varied 10% or more, depending upon the relative volatility of the monovalent higher molecular carboxylic acid and the volatility of the divalent higher molecular carboxylic acid. The more volatile of the two higher molecular carboxylic acids may be partially volatilized off with the still more volatile lower molecular carboxylic acids and/or with the alcoholic or aqueous liberating agents.

Generally speaking, the same metals may be used in the process of this invention with the possible exception of calcium. In my experiments I have found that the organometal resins hereof derived from calcium have such a high melting point it is difficult to carry the reaction to completion without decomposition. Thus, due to this difficulty, the novel organometal resins of this invention do not contemplate the inclusion of such resins derived from calcium.

For the most part, the new resins are soluble in mixtures of hydrocarbons with low boiling alcohols such as butanol. Their solutions, if applied in a thin layer, dry to a high gloss coating. The metals in these coatings may be the same or different, as pointed out in the various patents identified herein. Thin layers of these solutions dry extremely fast, especially if they contain divalent metals which may be converted into the trivalent state by oxygen, as is the case with iron. While a theoretical explanation of this unusual quality is not necessary, it may be visualized as set out below. In the DMOA's where iron is used, the compound would have the formula XFeOFeX. Thus, any oxidation is visualized as taking place intramolecularly in accordance with the formula

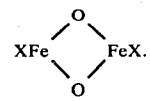

On the other hand, the oxidation of the new compounds of this invention are visualized as taking place as set out below for intramolecular oxidation is not possible:

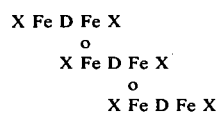

When the iron organometal compounds hereof are used in solutions, as set out above, in combination with DMOA's and applied in a thin coating, the dark coatings rapidly solidify forming a clear film of reddish-brown color. The color changes rapidly during the drying.

Where divalent metals are used which cannot oxidize to their trivalent state, the drying is somewhat less rapid, but coatings of such resinous materials are more flexible than those obtained from the DMOA's alone. Due to their drying characteristics, the preferred metals used in forming the metallic organo resins of this invention are iron, manganese, cobalt, nickel and chromium, but other metals such as zinc, lead, and etc. may be used as in my prior invention. Where necessary or desirable, metals which may exist only as divalent metals and metals which may exist as both divalent and trivalent metals may be used in combination as for instance as in XZnDFeX which is a stain of red-brown color with preservative activity.

In general, the condensed organometal acylates hereof may be used in the same way as my DMOA's, for instance, in paints, stains, inks and colorants for plastics. However, when the preferred metals or the preferred divalent acids or both are used, the acylates, in addition to other desirable characteristics, dry more quickly when solutions thereof are applied to substrates.

In a preferred embodiment of the invention, the dibasic acid used is dimer linoleic acid. This acid may be used per se, or it may be used in combination with other dibasic carboxylic acids; it is desirable not to use too great proportions of the other dibasic acids or the compounds may become insoluble. For instance, when using nonanedioic (azelaic) or decanedioic acids, not more than 50% of the amount of the dimer linoleic acid should be replaced, and when using the phthalic acids, not more than 25% should replace the dimer linoleic acids.

In considering the following purely illustrative embodiments of the invention, one must realize that the Examples are merely complementary to the patents previously discussed herein wherein reactants, other than the dibasic carboxylic, are set out and wherein reaction controls are fully set out. The completion of the reaction is determined in the same manner as in my previously issued patents.

Since the same high molecular monobasic carboxylic acid, or their esters with low molecular alcohols, can be used in the instant process as in my related processes, the illustrative monobasic acids have been selected which may be advantageously used with the preferred dibasic carboxylic acid, namely, dimer linoleic acid.

In the Examples, "tall oil fatty acids" refers to readily available fatty acid mixtures derived from tall oil. It is a mixture of fatty acids of 16–18 carbon atoms, consisting mostly of oleic and linoleic as obtained from tall oil. Essentially the same mixture can be obtained from soy bean oil and can be used in the same manner.

EXAMPLE 1

22.4 g iron powder is refluxed during five hours with 60 g acetic acid and 100 g water until all iron has gone into solution. Water and excess acid is distilled off and 112 g tall oil fatty acids are introduced slowly while distillation continues and the temperature rises to 150° C when 112 g dimer linoleic acid is introduced. Then the temperature is raised to 240° C and steam is blown in until no further distillation of acetic acid is observed. (Instead of steam, water may be dropped in.) Steaming is stopped and the batch is flushed with 20 g toluene to remove remnants of moisture. The resin (262 g) solidifies around 150° C and is dissolved in a mixture of xylene and butanol 1:1. When spread in a thin layer the solution dries tackfree within 5 minutes, while the dark color changes into a yellowish brown hue, which is transparent.

The formula may be visualized as X Fe D Fe X.

Using the same procedure but with 28 or 56 g dimer linoleic acid yields less-viscous and slightly slower-drying resins. One gets both X Fe D Fe X and X Fe O Fe X.

By replacing 56 g of the dimer with 20 g azelaic acid, a resin with a higher melting point is obtained with stronger color. In this modification, D's are derived from azelaic acid.

EXAMPLE 2

98 g manganese acetate is mixed with 112 g tall oil fatty acids and 112 g dimer linoleic acid, heated to 220° C and steamed until the acetic acid has been removed. The light brown resin dissolves in a mixture of toluene and butanol 2:1 and dries rapidly in a thin layer to a tough brown coating (transparent).

The formula for the Example may be visualized as: X Mn D Mn X.

EXAMPLE 3

32 g zincoxide is mixed with 112 g soybean fatty acid, 112 g dimer linoleic acid and 24 g acetic acid. At 170° C, steam is blown in and temperature raised to 240° C. The nearly colorless resin dissolves in a mixture of mineral spirits, xylene and butanol 10-5-10. It dries to a clear coating.

The formula for this Example may be visualized as: X Zn D Zn X.

EXAMPLE 4

100 g nickel acetate is mixed with 100 g dimer linoleic acid and 123 g tall oil fatty acids, heated to 240° C and steamed. A transparent light green resin results which dissolves in a mixture of xylene and isoamylalcohol.

The formula in this Example may be visualized as: X Ni D Ni X.

EXAMPLE 5

80 g copperacetate is heated with 112 g dimer linoleic acid and 112 g tall oil fatty acids to 180° C and treated with 40 g water. The yield is 244 g of a dark green resin soluble in xylene-butanol mixtures and usable as a preservative green stain for wood.

The formula in this Example may be visualized as: X Cu D Cu X.

Naphthenic acid may be used instead of tall oil fatty acids. Also, 28 g of dimer linoleic acid may be replaced with 16 g terephthalic acid.

EXAMPLE 6

100 g cobaltacetate is heated with 112 g ethylhexoic acid and 112 g dimer stearic acid to 200° C where steam is blown in. Part of the ethylhexoic acid distills off with acetic acid and steam, leaving a violet-blue resin (238g) which is a transparent wax.

The formula in this Example may be visualized as: X Co D Co X.

Instead of cobaltacetate, also cobalthydroxide with acetic acid can be used.

EXAMPLE 7

34 g chromousacetate is mixed with 56 g dimer linoleic acid and 56 g oleic acid and heated to 200° C where steam is blown in. The resulting resin when exposed in a thin layer dries rapidly to a transparent bright green coating.

The formula in this Example may be visualized as: X Cr D Cr X.

EXAMPLE 8

200 g ferrous oxide tallate T Fe O Fe T (T= tall oil fatty acid) is mixed with 10 g dimer linoleic acid and heated to 230° C. Condensation water is flushed out with 50 g mineral spirits. The drying time of a film of the resin is shortened by 75% when compared with the starting material. One obtains a solution of X Fe D Fe X in X Fe O Fe X in a molar ratio of about 1:9.

While this Example has shown the use of about 5% dimer linoleic acid, much larger percentages may be used relative to the quantity of MOA. However, the quantity of dimer linoleic acid used should not exceed 80% of the weight of MOA.

The invention and its advantages are apparent from the foregoing description. Various charges and modifications in the process and product may be made without departing from the spirit or scope of the invention or sacrificing unduly its material advantages.

I claim:

1. An oligomeric resin which is a divalent metal acylate of the formula:

X M D M X wherein:
   each X is an acyloxy ligand of a monobasic acid containing at least 7 carbon atoms;
   D is a diacyloxy ligand of a dibasic acid containing at least 8 carbon atoms; and
   M is a divalent metal atom other than calcium.

2. The resin of claim 1 wherein D is the ligand of nonanedioic acid.

3. The resin of claim 1 wherein D is the ligand of phthalic acid.

4. The resin of claim 1 wherein D is the ligand of dimer linoleic acid.

5. The resin of claim 1, wherein M is Mn.

6. The resin of claim 1, wherein M is Zn.

7. The resin of claim 1, wherein M is Ni.

8. The resin of claim 1, wherein M is Cu.

9. The resin of claim 1, wherein M is Co.

10. The resin of claim 1, wherein M is Cr.

11. The resin of claim 1, wherein M is Fe.

12. The resin of claim 1 wherein M is Fe, X is the ligand of fatty acid of at least 7 carbon atoms and D is the ligand of dimer linoleic acid.

13. In a process for preparing condensed oligomeric organo metallic resinous acylates containing divalent metals other than calcium wherein the acylate radical is a ligand of a monovalent high molecular carboxylic acid of at least 7 carbon atoms from (1) a monovalent high molecular carboxylic acid reactant containing said ligand and (2) uncondensed metal acylates of monovalent low molecular volatile carboxylic acids of at most 5 carbon atoms per se of the formula $M(X')_2$ wherein M is said metal and $X'$ is the acylate ligand of a monovalent carboxylic acid of at most 5 carbon atoms, or said uncondensed metal acylates formed in situ under severe reaction conditions of heating to 180° C and above and with the aid of liberating agents selected from the group consisting of water and volatile low molecular monovalent alcohols whereby said low molecular monovalent carboxylic acid or its ester with a low molecular volatile monovalent alcohol is vaporized off, the modification comprising including in said process a divalent carboxylic acid reactant of at least 6 carbon atoms thereby producing an oligomeric resinous divalent metal acylate of the formula: X M D M X, wherein each X is an acyloxy ligand of a monobasic acid containing at least 7 carbon atoms, D is a diacyloxy ligand of a dibasic acid containing at least 6 carbon atoms; and M is a divalent metal atom other than calcium.

14. The process of claim 13 wherein the molar ratio of said higher molecular monovalent carboxylic acid reactant and said divalent carboxylic reactant is approximately 2:1.

15. The process of claim 13 wherein the molar ratio of said higher molecular monovalent carboxylic acid reactant and said divalent carboxylic acid reactant is in excess of approximately 2:1.

16. The proces of claim 13 wherein said divalent carboxylic acid is dimer linoleic acid.

* * * * *